United States Patent [19]
Dean et al.

[11] Patent Number: 6,019,958
[45] Date of Patent: *Feb. 1, 2000

[54] TECHNETIUM-99M LABELED PEPTIDES FOR IMAGING INFLAMMATION

[75] Inventors: Richard T. Dean; Brian R. Moyer, both of Bedford, N.H.

[73] Assignee: Diatide, Inc., Londonderry, N.H.

[ * ] Notice: This patent is subject to a terminal disclaimer.

[21] Appl. No.: 08/564,315

[22] PCT Filed: May 25, 1994

[86] PCT No.: PCT/US94/05895

§ 371 Date: Oct. 4, 1996

§ 102(e) Date: Oct. 4, 1996

[87] PCT Pub. No.: WO94/28942

PCT Pub. Date: Dec. 22, 1994

Related U.S. Application Data

[63] Continuation-in-part of application No. 08/480,551, Jun. 7, 1995, Pat. No. 5,811,394, which is a continuation of application No. 08/264,176, Jun. 22, 1994, abandoned, which is a continuation of application No. 07/653,012, Feb. 8, 1991, abandoned.

[51] Int. Cl.[7] .......................... A61K 38/00; A61K 51/00; C07F 13/00
[52] U.S. Cl. ........................ 424/1.69; 530/300; 530/326; 436/808; 514/54; 534/10; 534/14
[58] Field of Search ................................ 424/1.41, 1.53, 424/1.69; 514/54; 530/300, 326; 534/10, 14; 436/808

[56] References Cited

U.S. PATENT DOCUMENTS

| | | | |
|---|---|---|---|
| 4,057,617 | 11/1977 | Abramovici et al. | 424/1.69 |
| 4,385,046 | 5/1983 | Milbrath et al. | 424/1.73 |
| 4,434,151 | 2/1984 | Byrne et al. | 424/1.65 |
| 4,444,690 | 4/1984 | Fritzberg et al. | 534/14 |
| 4,472,509 | 9/1984 | Gansow et al. | 436/548 |
| 4,571,430 | 2/1986 | Byrne et al. | 560/148 |
| 4,575,556 | 3/1986 | Byrne et al. | 549/63 |
| 4,578,079 | 3/1986 | Ruoslhati et al. | 623/11 |
| 4,792,525 | 12/1988 | Ruoslhati et al. | 435/402 |
| 4,857,508 | 8/1989 | Adams et al. | 514/18 |
| 4,861,869 | 8/1989 | Nicolotti et al. | 424/1.53 |
| 4,877,868 | 10/1989 | Reno et al. | 530/391.5 |
| 4,935,223 | 6/1990 | Phillips | 424/1.17 |
| 4,952,562 | 8/1990 | Klein et al. | 514/18 |
| 4,986,979 | 1/1991 | Morgan et al. | 424/1.17 |

(List continued on next page.)

FOREIGN PATENT DOCUMENTS

| | | |
|---|---|---|
| 0055028 | 6/1982 | European Pat. Off. . |
| 0063002 | 10/1982 | European Pat. Off. . |
| 0108406 | 5/1984 | European Pat. Off. . |
| 0135160 | 3/1985 | European Pat. Off. . |
| 0137457 | 4/1985 | European Pat. Off. . |
| 0188256 | 10/1986 | European Pat. Off. . |
| 0284071 | 9/1988 | European Pat. Off. . |
| 301458A2 | 2/1989 | European Pat. Off. . |
| 0398143 | 11/1990 | European Pat. Off. . |
| 410537A1 | 1/1991 | European Pat. Off. . |

(List continued on next page.)

OTHER PUBLICATIONS

Ronco et al. (1991) Int. J. Artif. Organs 14:457–462.

Baidoo et al., "Synthesis of a Diaminedithiol Bifunctional Chelating Agent for Incorporation of Technetium–99m Into Biomolecules," *Bioconjugate Chemistry* 1(2):132–137 (1990).

Bebawy et al., "In Vitro Effect of Platelet Factor 4 on Normal Human Neutrophil Functions," 1986, *J. Leukocyte Biol.* 39:423–434.

Ben–Haim et al., "The Safety and Pharmacokinetics in Adult Subjects of an Intravenously Administered $^{99m}$Tc–labeled 17 Amino Acid Peptide (CYT–379)," *Nucl. Med. Biol.* 21(2): 131–142 (1994).

Bryson et al., 1988, "Neutral Technetium(V) Complexes with Amide–Thiol–Thioether Chelating Ligands", *Inorg. Chem.* 27:2154–2161.

Bryson et al., 1990, "Protecting Groups in the Preparation of Thiolate Complexes of Technetium", *Inorg. Chem.* 29:2948–2951.

Byrne and Tolman, 1983, "Technetium–99m Bifunctional Chelating Agent—Thiolactone for Coupling to Biomolecules, $N_2S_2$ Ligand for Chelatoin to Technetium", *J. Nucl. Med.* 24:P126.

Yamamura, "Preparation of cysteine–containing pentapeptide as a ligand for peptide–metal complexes," *Chemical Abstracts* 114:850, abstract No. 186080b (1991).

Davison et al., 1981, "A New Class of Oxotechnetium(5+) Chelate Complexes containing a $TcON_2S_2$ Core", *Inorg. Chem.* 20: 1629–1632.

Deuel et al., "Amino Acid sequence of human platelet factor 4," 1977, *Proc. Natl. Acad. Sci. USA* 74: 2256–2258.

(List continued on next page.)

*Primary Examiner*—Lila Feisee
*Assistant Examiner*—Michael Pak
*Attorney, Agent, or Firm*—Patricia A. McDaniels; Kevin E. Noonan

[57] ABSTRACT

This invention relates to compositions that are radiolabeled scintigraphic imaging agents, comprising a polybasic compound covalently linked to a radiolabel binding moiety and the composition further comprising a polysulfated glycan. The invention also provides methods for producing and using such compositions. Specifically, the invention relates to compositions comprised of technetium-99m (Tc-99m) labeled scintigraphic imaging agents comprising a polybasic compound having at least 5 chemical functionalities that are basic at physiological pH and a radiolabel-binding moiety, the composition further comprising a polysulfated glycan, the composition being capable of accumulating at inflammatory sites in vivo. Methods and kits for making such compositions, and methods for using such compositions to image sites of infection and inflammation in a mammalian body, are also provided.

30 Claims, 1 Drawing Sheet

U.S. PATENT DOCUMENTS

| | | | |
|---|---|---|---|
| 5,086,069 | 2/1992 | Klein et al. | 514/399 |
| 5,198,424 | 3/1993 | McEver | 514/13 |
| 5,266,562 | 11/1993 | Mukherjee et al. | 514/15 |
| 5,308,603 | 5/1994 | Thakar | 424/1.49 |
| 5,376,356 | 12/1994 | Morgan, Jr. | 424/1.41 |
| 5,561,220 | 10/1996 | Dean et al. | 424/1.69 |

FOREIGN PATENT DOCUMENTS

| | | |
|---|---|---|
| 410539A1 | 1/1991 | European Pat. Off. . |
| 410540A1 | 1/1991 | European Pat. Off. . |
| 410541A1 | 1/1991 | European Pat. Off. . |
| 422937A1 | 4/1991 | European Pat. Off. . |
| 422938A1 | 4/1991 | European Pat. Off. . |
| 425212A2 | 5/1991 | European Pat. Off. . |
| 0453082 | 10/1991 | European Pat. Off. . |
| 478328A1 | 4/1992 | European Pat. Off. . |
| 502536 | 9/1992 | European Pat. Off. . |
| 513810 | 11/1992 | European Pat. Off. . |
| 512829 | 11/1993 | European Pat. Off. . |
| WO8902752 | 4/1989 | WIPO . |
| WO8905150 | 6/1989 | WIPO . |
| WO8910759 | 11/1989 | WIPO . |
| WO9010463 | 9/1990 | WIPO . |
| WO9015818 | 12/1990 | WIPO . |
| WO9101331 | 2/1991 | WIPO . |
| WO9115515 | 10/1991 | WIPO . |
| WO9117173 | 11/1991 | WIPO . |
| WO9202240 | 2/1992 | WIPO . |
| WO9205154 | 4/1992 | WIPO . |
| WO9213572 | 8/1992 | WIPO . |
| WO9217492 | 10/1992 | WIPO . |
| WO9300095 | 1/1993 | WIPO . |
| WO9308174 | 4/1993 | WIPO . |
| WO9310747 | 6/1993 | WIPO . |
| WO9317719 | 9/1993 | WIPO . |
| WO9321962 | 11/1993 | WIPO . |
| WO9323085 | 11/1993 | WIPO . |
| WO9325244 | 12/1993 | WIPO . |
| WO9407918 | 4/1994 | WIPO . |
| WO9423758 | 10/1994 | WIPO . |

OTHER PUBLICATIONS

Deuel et al., "Platelet factor 4 is chemotactic for neutrophils and monocytes," 1981, *Proc. Natl. Acad. Sci. USA* 78:4584–4587.

Ebright et al., "The gallium scan: Problems and misuse in examination of patients with suspected infections," *Arch. Int. Med.* 142:246–254 (1982).

Fischman et al., "Imaging Focal Sites of Bacerial Infection in Rats with Indium–111–Labeled Chemotactic Peptide Analogs," 1991, *J. Nucl. Med.* 32:482–491.

Fritzberg et al., 1982, "Clinical comparison of Tc–99m N,N',–bis(mercaptoacetamido)ethylenediamine and ($^{131}$I)ortho–iodohippurate for evaluation of renal tubular function: Concise Communication", *J. Nucl. Med.* 23:P17.

Fritzberg et al., 1982, "Synthesis and Biological Evaluation of Tc–99m N,N–Bix(mercaptoacetyl)–2,3–diaminopropanoate: A Potential Replacement for [$^{131}$I]o–iodohippurate", *J. Nucl. Med.* 23: 592–598.

Goldman et al., Inhibition of human neutrophil receptor–mediated uptake of N–Formyl–Met–Leu–Phe by platelet factor 4 (59–70), 1985, *Immunol.* 54: 163–171.

Hartman et al., 1992, "Non–peptide fibrinogen receptor antagonists: 1. Discovery and design of exosite inhibitors", *J. Med. Chem.* 35: 4640–4642.

Holt & Niewiarowski, "Biochemistry of α Granule Proteins," 1985, *Sem. Hematol.* 22: 151–163.

Jiang et al., "Localization of Abscess with an Iodinated Synthetic Chemotactic Peptide," 1982, *Nuklearmedizin* 21: 110–113.

Khaw et al., 1982, "Technetium–99m Labeling of Antibodies to Cardiac Myosin Fab and Human Fibrinogen", *J. Nucl. Med.* 23: 1011–1019.

Knight et al., "Evaluation of TC–99m Labeled Cyclic Peptides for Thrombus Imaging," *The Journal of Nuclear Medicine* 34(5):17P–18P (1993).

Knight et al., 1990, "Thrombus Imaging with Tc–99m Synthetic peptides Reactive with Activated Platelets", *J. Nucl. Med.* 31:757#209.

Knight, 1990, "Radiopharmaceuticals for Thrombus Detection", *Sem. Nucl. Med.* 20:52–67.

LaMuraglis et al., "Utility of the indium 111–labeled human immunoglobulin G scan for the detection of focal vascular graft infection," 1989, *J. Vasc. Surg.* 10:20–28.

Li et al., "A new bifunctional chelating agent alpha, xi–N, N'–bis(L–cysteinyl)–L–lysine for radiolabeling of monoclonal antibodies with technetium–99m," *Chemical Abstracts* 115:2001, abstract No. 159733f (1991).

Li et al., "A New Bifunctional Chelating Agent N,N'–BIS–(L–Cysteinyl)–L–Lysine for Radiolabelling of Monoclonal Antibodies with Technetium–99m," *Chinese Chemical Letters* 2(4):285–288 (1991).

Lind et al., "Immunoscintigraphy of Inflammatory Process with a Technetium–99m–Labeled Monoclonal Antigranulocyte Antibody (Mab BW 250/183)," 1990, *J. Nucl. Med.* 31:417–473.

Loscalzo et al., "The Interaction of Platelet Factor Four and Glycosaminoglycans," 1985, *Arch. Biochem. Biophys.* 240:446–455.

Maione et al., "Inhibition of Angiogenesis by Recombinant Human Platelet Factor–4 and Related Peptides," 1989, *Science* 247:77–79.

Niedel and Cuatrecasas, 1980, "Formyl Peptide Chemotactic Receptors of Leukocytes and Macrophages," in *Curr. Top. Cell. Reg.* 17: 137–170.

Ojima et al., 1992, "Design and Synthesis of New RGD Peptides as Inhibitors of Human Platelet Aggregation", *204th Meeting, Amer. Chem. Soc.* Abst. 44.

Osterman et al., "The Carboxyl–Terminal Tridecapeptide of Platelet Factor 4 Is A Potent Chemotactic Agent for Monocytes," 1982, *Biochem. Biophys. Res. Comm.* 107: 130–135.

Parise & Phillips, "Reconstitution of the Purified Platelet Fibrinogen Receptor: Fibrinogen Binding Properties of the Glycoprotein 11b–111a Complex," *J. Biol. Chem.* 260:10698–10707 (1985).

Peters, "Imaging Inflammation: Current role of labeled autologous leukocytes," *J. Nucl. Med.* 22:65–67 (1992).

Plow et al., "Interaction of Adhesive Proteins With Platelets: Common Features With Distinct Differences," 1987, in *Perspectives in Inflammations, Neoplasia and Vascular Cell Biology*, pp. 267–275.

Rhodes, 1974, "Considerations in the Radiolabeling of Albumin", *Sem. Nucl. Med.* 4: 281–293.

Rucinski et al., "Human Platelet Factor 4 and Its C–Terminal Peptides: Heparin Binding and Clearance From the Circulation," *Thrombosis and Haemostasis* 63(3):493–498 (1990).

Doi et al., "Structure of the Rat Platelet Factor 4 Gene: a Marker for Megakaryocyte Differentiation," *Molecular & Cellular Biology* 7(2):898–704 (1987).

Vorne et al., "Technetium–99m HM–PAO–Labeled Leukocytes in Detection of Inflammatory Lesions: Comparison with Gallium–67 Citrate," 1989, *J. Nucl. Med.* 30:1332–1336.

Wilkinson, "Chemotactic Factors: An Overview," 1988, *Meth. Enzymol.* 162: 127–132.

Zoghbi et al., "Selective Cell Labeling: A Potential Radioactive Agent for Labeling Human Neutrophils," 1981, *J. Nucl. Med.* 22: 32 (Abst).

FIG. 1

TECHNETIUM-99M LABELED PEPTIDES FOR IMAGING INFLAMMATION

This application is a continuation-in-part of allowed U.S. patent application Ser. No. 08/480,551, filed Jun. 7, 1995 now U.S. Pat. No. 5,811,394; which is a continuation of U.S. patent application Ser. No. 08/264,176, filed Jun. 22, 1994 and now abandoned; which is a continuation of U.S. patent application Ser. No. 07/653,012, filed Feb. 8, 1991 and now abandoned.

BACKGROUND OF THE INVENTION

1. Field of the Invention

This invention relates to compositions that are radiolabeled scintigraphic imaging agents, methods of using these compositions and methods for producing such radiolabeled compositions. Specifically, the invention relates to technetium-99m labeled scintigraphic imaging agents that are compositions of a polysulfated glycan or mixture thereof and a compound comprising a polybasic moiety covalently linked to a radiolabel binding moiety radiolabeled with technetium-99m (Tc-99m). Methods and kits for making such compositions, and methods for using such compositions to image sites of infection and inflammation in a mammalian body are also provided.

2. Description of the Prior Art

There is a clinical need to be able to determine the location and/or extent of sites of focal or localized infection and inflammation. In a substantial number of cases conventional methods of diagnosis (such as physical examination, x-ray, CT and ultrasonography) fail to identify such sites (e.g., an abscess). Although biopsy may be resorted to, it is preferable to avoid such invasive procedures, at least until they are diagnostically appropriate to identify the pathogen responsible for an abscess at a known location. Identifying the site of such "occult" infection is important because rapid localization and identification of the problem is critical to effective therapeutic intervention.

In the field of nuclear medicine, certain pathological conditions can be localized or the extent of such conditions determined by imaging the internal distribution of administered radioactively-labeled tracer compounds (i.e. radiotracers or radiopharmaceuticals) that accumulate specifically at the pathological site. A variety of radionuclides are known to be useful for radioimaging, including $^{67}$Ga, $^{99m}$Tc (Tc-99m), $^{111}$In, $^{123}$I, $^{125}$I, $^{169}$Yb and $^{186}$Re.

However, an abscess may be caused by any one of many possible pathogens, so that a radiotracer specific for a particular pathogen would have limited scope. On the other hand, infection is almost invariably accompanied by inflammation, which is a general response of the body to tissue injury. Therefore, a radiotracer specific for sites of inflammation would be expected to be useful in localizing sites of infection caused by any pathogen, as well as being useful for localizing other inflammatory sites.

One of the main phenomena associated with inflammation is the localization of leukocytes (white blood cells), usually monocytes and neutrophils, at the site of inflammation. A radiotracer specific for leukocytes would be useful in detecting leukocytes at the site of a localized infection. Currently approved nuclear medicine procedures for imaging sites of infection use either indium-111 labeled leukocytes ($^{111}$In-WBC) (see, e.g. Peters, 1992, *J. Nucl. Med.* 33: 65–67) or gallium-67 ($^{67}$Ga) citrate (see, e.g. Ebright et al., 1982, *Arch. Int. Med.* 142: 246–254). A major disadvantage of using $^{111}$In-labeled WBCs is that the preparation of the radiotracer requires a number of technical steps: sterile removal of autologous blood, sterile isolation of the leukocytes from the blood, sterile labeling of the leukocytes using conditions that do not damage the cells (since damaged WBC are taken up by the reticuloendothelial system when re-injected) and sterile return (re-injection) of the (now labeled) leukocytes to the patient. Furthermore, a delay of 12 to 48 hours between injection and imaging may be required to obtain optimum imaging. While Tc-99m labeled leukocytes have been used to shorten this delay period (see, e.g. Vorne et al., 1989, *J. Nucl. Med.* 30: 1332–1336), ex-corporeal labeling is still required. A preferred radiotracer would be one that either would label leukocyes in whole blood or would not require removal and manipulation of autologous blood components ex corpora.

Alternatively, $^{67}$Ga-citrate can be administered by intravenous injection. However, this compound is not specific for sites of infection or inflammation. Moreover, a delay of up to 72 hours is often required between injection of the radiotracer and imaging. In addition, the γ-(gamma) emissions energies of $^{67}$Ga are not well suited to conventional gamma cameras.

Radiolabeled monoclonal and polyclonal antibodies raised against human leukocytes (including monocytes, neutrophils, granulocytes and other cell types) have been developed. Tc-99m labeled antigranulocyte monoclonal antibodies (see, e.g. Lind et al., 1990, *J. Nucl. Med.* 31: 417–473) and $^{111}$In-labeled non-specific human immunoglobulin (see, e.g. LaMuraglia et al., 1989, *J. Vasc. Surg.* 10: 20–28) have been tested for the detection of inflammation secondary to infection. $^{111}$In-labeled IgG shares the disadvantages of $^{111}$In-labeled WBC, in that 24–48 hours are required between injection and optimal imaging. In addition, radiolabeled antibodies are difficult to produce and face protracted approval procedures, as they are routinely classified as biologics by regulatory agencies.

Small, readily synthesized molecules are preferred as routinely-used radio-pharmaceuticals. There is clearly a need for small synthetic molecules that can be used either to label leukocytes in whole blood (i.e., without the need to isolate the leukocytes from the other components of whole blood) or that can be directly injected into a patient and will image sites of infection and inflammation by localizing at sites where leukocytes have accumulated.

One kind of small, readily synthesized molecule useful in such applications are peptides. The sensitivity of imaging methods using radioactively-labeled peptides is much higher than other techniques known in the art, since the specific binding of the radioactive peptide concentrates the radioactive signal over the area of interest, for example, an inflammatory site. In addition, methods for achieving high-yield chemical synthesis of small peptides are well known in the art.

Radiolabeled peptides, and in particular formyl-methionyl-leucyl-phenylalanyl (fMLF)-containing peptides, have been reported in the prior art.

Zoghbi et al., 1981, *J. Nucl. Med.* 22: 32 (Abst) disclose formyl peptide chemotactic factors (fMLF) derived from bacteria coupled to $^{111}$In-labeled transferrin.

Jiang et al., 1982, *Nuklearmedizin* 21: 110–113 disclose a chemotactic formylated peptide (fMLF) radiolabeled with $^{125}$I.

Fischman et al., 1991, *J. Nucl. Med.* 32: 482–491 relates to chemotactic formyl peptide (fMLF)—$^{111}$In-labeled DTPA conjugates.

EPC 90108734.6 relates to chemotactic formyl peptide (fMLF)—$^{111}$In-labeled DTPA conjugates.

U.S. Pat. No. 4,986,979 relates to the use of radiolabeled chemotactic formyl peptides (fMLF) to radiolabel leukocytes ex-corporeally via a photoaffinity label.

PCT WO90/10463 relates to the use of radiolabeled chemotactic formyl peptides (fMLF) to radiolabel leukocytes ex-corporeally via a photoaffinity label.

The use of labeled fMLF peptides known in the aforementioned art suffers from the serious drawback that this peptide causes adverse physiological responses such as superoxide release from neutrophils (Niedel and Cuatrecasas, 1980, Formyl Peptide Chemotactic Receptors of Leukocytes and Macrophages, in *Curr. Top. Cell. Reg.* 17: 137–170), and at sufficient doses these compounds can cause leukocytopenia (Jiang et al., 1982, *Nuklearmed.* 21: 110–113).

Another source of inflammatory site-specific peptides is platelet factor 4, a naturally-occurring chemotactic peptide, consisting of 70 amino acids having a molecular weight of 7800 daltons and known in the prior art to bind to neutrophils and monocytes, cell types known to be associated with sites of inflammation and infection in vivo. Of interest with regard to the present invention, the carboxyl terminus of PF4 is known to bind to polysulfated glycans such as heparin (Loscalzo et al., 1985, *Arch. Biochem. Biophys.* 240: 446–455). In addition, an advantage of PF4 over the fMLF compounds known in the art is that it does not cause superoxide release from neutrophils even at concentrations of 20 $\mu$M (Bebawy et al., 1986, *J. Leukocyte Biol.* 39: 423–434).

Thorbecke & Zucker, 1989, European Patent Application No. 88111962.2 disclose compositions and methods for modulating immune responses comprising administering an immunomodulating amount of platelet factor 4 or peptides derived therefrom.

Deuel et al., 1977, *Proc. Natl. Acad. Sci. USA* 74: 2256–2258 disclose the amino acid sequence of human platelet factor 4.

Deuel et al., 1981, *Proc. Natl. Acad. Sci. USA* 78: 4584–4587 disclose that platelet factor 4 is chemotactic for neutrophils and monocytes in vitro.

Osterman et al., 1982, *Biochem. Biophys. Res. Comm.* 107: 130–135 disclose that the carboxyl-terminal tridecapeptide of platelet factor 4 has chemotactic properties.

Holt & Niewiarowski, 1985, *Sem. Hematol.* 22: 151–163 provide a review of the biochemistry of platelet $\alpha$-granule proteins, including platelet factor 4.

Goldman et al., 1985, *Immunol.* 54: 163–171 reveal that fMLF receptor-mediated uptake is inhibited in human neutrophils by platelet factor 4 and a carboxyl-terminal dodecapeptide thereof.

Loscalzo et al., ibid., describe the biochemical interaction between platelet factor 4 and glycosaminoglycans such as heparin.

Bebawy et al., ibid., describe the platelet factor 4-mediated chemotactic response of neutrophils in vitro.

Maione et al., 1989, *Science* 247: 77–79 disclose that angiogenesis is inhibited by recombinant human platelet factor 4 and peptide fragments thereof.

The use of chelating agents for radiolabeling polypeptides, and methods for labeling peptides and polypeptides with Tc-99m are known in the prior art and are disclosed in co-pending U.S. patent application Ser. No. 07/653,012, now abandoned, which issued as U.S. Pat. No. 5,654,272; Ser. No. 07/807,062, now U.S. Pat. No. 5,443,815; Ser. No. 07/871,282, a divisional of which issued as U.S. Pat. No. 5,720,934; Ser. No. 07/886,752, now abandoned, a continuation of which has been allowed as U.S. Ser. Nos. 08/273,274; 07/893,981, now U.S. Pat. No. 5,508,020; Ser. No. 07/955,466; Ser. No. 08/019,864, now U.S. Pat. No. 5,552,525; Ser. No. 08/044,825, now abandoned, which issued as U.S. Pat. No. 5,645,815; and Ser. No. 08/073,577, now U.S. Pat. No. 5,561,220; and PCT International Applications PCT/US92/00757, PCT/US92/10716, PCT/US93/02320 and PCT/US93/04794, which are hereby incorporated by reference.

SUMMARY OF THE INVENTION

The present invention provides scintigraphic imaging agents that are compositions comprising radioactively-labeled reagents and polysulfated glycans. The compositions of the invention accumulate at sites of inflammation in vivo. The reagents comprising the compositions of the invention are themselves comprised of polybasic compounds that are capable of specifically localizing at sites of infection or inflammation or components thereof, wherein said compounds are covalently linked to radioisotope, preferably technetium-99m, binding moieties.

It has unexpectedly been found that the combination of a Tc-99m radiolabeled polybasic compound and a polysulfated glycan as provided by the present invention advantageously enables the acquisition of scintigraphic images of focal sites of infection and inflammation in vivo. Administration of this combination results in a greater degree of localization of the Tc-99m radioactive signal at the site of infection when compared to administration of the Tc-99m labeled polybasic compound alone. As a result, such scintigraphic images produced by this combination are superior to the images obtained using Tc-99m labeled scintigraphic imaging agents comprising the radiolabeled polybasic compound alone (see Example 3 and Table II hereinbelow). Higher ratios of the detected radioactivity at infection site versus blood and infection site versus normal tissue are also found using the compositions of the invention compared with the radiolabeled compounds alone.

Accordingly, the invention provides radiolabeled compositions that accumulate at sites of inflammation in vivo, methods for preparing such compositions, and methods for using such radiolabeled compositions for imaging sites of infection and inflammation within a mammalian body.

In a first aspect of the present invention, scintigraphic imaging agents for imaging sites of inflammation within a mammalian body are provided, comprising compositions that comprise a technetium-99m labeled reagent having a molecular weight of about 500 daltons to about 15,000 daltons and having at least 5 residues that are basic at physiological pH, covalently linked to a technetium-99m binding moiety, the composition further comprising a polysulfated glycan having a molecular weight of at least about 1000 daltons, wherein the reagent is radioactively labeled with technetium-99m, and wherein the composition is capable of accumulating at sites of inflammation in vivo. In preferred embodiments, the reagent is a peptide of 5 to 100 amino acids that is platelet factor 4 or a fragment or analog thereof. In other preferred embodiments, the polysulfated glycan is heparin, heparan sulfate, dextran sulfate, chondroitin sulfate, dermatan sulfate or derivatives thereof.

In a second aspect of the invention, Tc-99m labeled reagents are provided as components of the scintigraphic imaging agents of the invention, wherein the reagents are comprised of polybasic compound, preferably a platelet factor 4-derived peptide of fragment thereof, covalently linked to a radiolabel-binding moiety of formula $$Cp(aa)Cp \qquad \text{I.}$$

wherein Cp is a protected or unprotected cysteine residue and (aa) stands for an amino acid, and wherein the radiolabel-binding moiety is covalently linked to the polybasic compounds. In a preferred embodiment, the amino acid is glycine. In another preferred embodiment, the radiolabel-binding moiety is linked to the polybasic compound via from about one to about 20 amino acids.

In a third aspect, a component of the scintigraphic imaging agents provided by the invention are reagents comprising a polybasic compound, preferably a platelet factor 4-derived peptide of fragment thereof, covalently linked to a radiolabel-binding moiety comprising a single thiol moiety having the following structure:

$$A\text{—}CZ(B)\text{—}[C(R^1R^2)]_n\text{—}X \qquad \text{II.}$$

wherein A is H, HOOC, H$_2$NOC, (peptide)-NHOC, (peptide)-OOC or R$^4$; B is H, SH or —NHR$^3$, —N(R$^3$)-(peptide) or R$^4$; Z is H or R$^4$; X is SH or —NHR$^3$, —N(R$^3$)-(peptide) or R$^4$; R$^1$, R$^2$, R$^3$ and R$^4$ are independently H or straight or branched chain or cyclic lower alkyl; n is 0, 1 or 2; and: (1) where B is —NHR$^3$ or —N(R$^3$)-(peptide), X is SH and n is 1 or 2; (2) where X is —NHR$^3$ or —N(R$^3$)-(peptide), B is SH and n is 1 or 2; (3) where B is H or R$^4$, A is HOOC, H$_2$NOC, (peptide)-NHOC, (peptide)-OOC, X is SH and n is 0 or 1; (4) where A is H or R$^4$, then where B is SH, X is —NHR$^3$ or —N(R$^3$)-(peptide) and where X is SH, B is —NHR$^3$ or —N(R$^3$)-(peptide); (5) where X is H or R$^4$, A is HOOC, H$_2$NOC, (peptide)-NHOC, (peptide)-OOC and B is SH; (6) where Z is methyl, X is methyl, A is HOOC, H$_2$NOC, (peptide)-NHOC, (peptide)-OOC and B is SH and n is 0; and wherein the thiol moiety is in the reduced form.

In another embodiment are provided components of the scintigraphic imaging agents of the invention comprising a reagent comprised of a polybasic compound, preferably a platelet factor 4-derived peptide of fragment thereof, covalently linked to a radiolabel-binding moiety of formula:

III.

[for purposes of this invention, radiolabel-binding moieties having this structure will be referred to as picolinic acid (Pic)-based moieties]; or

IV.

[for purposes of this invention, radiolabel-binding moieties having this structure will be referred to as picolylamine (Pica)-based moieties]; wherein X is H or a protecting group; (amino acid) is any amino acid; the radiolabel-binding moiety is covalently linked to the peptide and the complex of the radiolabel-binding moiety and the radiolabel is electrically neutral. In a preferred embodiment, the amino acid is glycine and X is an acetamidomethyl protecting group. In additional preferred embodiments, the polybasic compound is covalently linked to the radiolabel-binding moiety via an amino acid, most preferably glycine, and the radiolabel is technetium-99m.

In yet another embodiment of the invention, components of the radiolabeled scintigraphic imaging agents of the invention are provided that are reagents comprising a polybasic compound, preferably a platelet factor 4-derived peptide or fragment thereof, and a bisamino bisthiol radiolabel-binding moiety covalently linked to the polybasic compound. The bisamino bisthiol radiolabel-binding moiety in this embodiment of the invention has a formula selected from the group consisting of:

V.

wherein each R$^5$ can be independently H, CH$_3$ or C$_2$H$_5$; each (pgp)$^s$ can be independently a thiol protecting group or H; m, n and p are independently 2 or 3; A is linear or cyclic lower alkyl, aryl, heterocyclyl, combinations or substituted derivatives thereof; and X is peptide;

VI.

wherein each R$^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-peptide; R$^6$ is H or peptide; provided that when V is H, R$^6$ is peptide and when R$^6$ is H, V is peptide. [For purposes of this invention, radiolabel-binding moieties having these structures will be referred to as "BAT" moieties]. In a preferred embodiment, the polybasic compound is covalently linked to the radiolabel-binding moiety via an amino acid, most preferably glycine.

The invention also comprises kits for preparing the compositions of the invention, methods for radiolabeling the reagents of the invention with Tc-99m and methods for using the radiolabeled compositions for imaging sites of infection or inflammation in mammalian body by gamma scintigraphy.

The invention provides compositions that are scintigraphic imaging agents comprising complexes of the radiolabel binding moiety of the reagents of the invention with Tc-99m. Methods for radiolabeling these reagents with Tc-99m are also provided. Radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling by ligand exchange of a prereduced Tc-99m complex as provided herein.

The invention also provides kits for preparing scintigraphic imaging agents that are a composition comprising a polysulfated glycan and Tc-99m labeled reagents of the invention. Kits for preparing the scintigraphic imaging agents of the invention, wherein the radiolabel is Tc-99m, are comprised of a first sealed vial containing a predetermined quantity of an unlabeled embodiment of a reagent of the invention and a sufficient amount of reducing agent to label the reagent with technetium-99m, and a second sealed vial containing a predetermined quantity of the polysulfated glycan of the invention. Compositions of the invention are then made by labeling the contents of the first vial with technetium-99m and then mixing the contents of the first vial with the contents of the second vial to provide the composition. Alternatively, appropriate amounts of the unlabeled reagent and the polysulfated glycan can be contained in a single vial. In preferred embodiments, the polysulfated glycan is heparin, heparan sulfate, dextran sulfate, chondroitin sulfate, dermatan sulfate or derivatives thereof.

This invention provides methods for preparing peptide embodiments of the scintigraphic imaging agents of the invention by chemical synthesis in viro. In a preferred embodiment, peptides are synthesized by solid phase peptide synthesis.

This invention provides methods for using compositions comprising Tc-99m labeled scintigraphic imaging agents for imaging sites of inflammation and infection within a mammalian body by obtaining in vivo gamma scintigraphic images. These methods comprise administering an effective diagnostic amount of a Tc-99m labeled composition and detecting the gamma radiation emitted by the Tc-99m label localized at the inflammation site within the mammalian body.

Methods are also provided for specifically radiolabeling whole blood and using mixtures comprising radiolabeled whole blood to image sites of inflammation within a mammalian body. One such embodiment comprises mixing whole blood with an amount, preferably from about 1 microgram to 100 milligrams, of a polysulfated glycan to form a mixture. A radiolabeled whole blood mixture is then formed by adding an amount, from about 1 microgram to 100 milligrams, of a radiolabeled, preferably Tc-99m labeled, composition of matter that is a reagent comprising a polybasic moitey covalently linked to a radiolabel binding moiety, to the first whole blood mixture. This radiolabeled whole blood mixture is then administered to an animal such as a human being having or suspected of having a site of inflammation in vivo, and the radioactive signal detected to localize the site of inflammation as described herein. This method provides an advantage over methods for labeling leukocytes known in the prior art, since the instant method eliminates the need for isolation of leukocytes from whole blood and attendant extensive ex corpora manipulation of whole blood.

The reagents of the invention may also be comprised of a polyvalent linking moiety. Polyvalent linking moieties of the invention are comprised of at least 2 identical linker functional groups capable of covalently bonding to polybasic compounds or Tc-99m binding moieties. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl)benzoic acid (DMAB), N-[2-(N',N'-bis(2-succinimidoethyl)aminoethyl)]-$N^6,N^9$-bis(2-methyl-2-mercaptopropyl)-6,9-diazanonanamide (BAT-BS), tris(succinimidylethyl)amine (TSEA), bis-succinimidohexane (BSH), 4-(O—$CH_2$CO-Gly-Gly-Cys.amide)acetophenone (ETAC), tris(acetamidoethyl) amine, bis(acetamidomethyl)amine, bis(acetamidoethyl)amine, $\alpha,\epsilon$-bis(acetyl)lysine, lysine, 1,8-bis-acetamido-3,6dioxa-octane or a derivative thereof.

Specific preferred embodiments of the present invention will become evident from the following more detailed description of certain preferred embodiments and the claims.

DETAILED DESCRIPTION OF THE INVENTION

The present invention provides scintigraphic imaging agents for imaging target sites within a mammalian body that accumulate at sites of inflammation comprising compositions of Tc-99m labeled reagents and polysulfated glycans. The reagents of the compositions of the invention comprise polybasic compounds that are covalently linked to a radiolabel binding moiety wherein the radiolabel binding moiety binds a radioisotope. For the purposes of this invention, the term "polybasic compound" is intended to encompass chemical compounds having at least 5 chemical functionalities that are basic and are cationic at physiological pH (i.e. about pH 7.0±0.5), for example but not limited to, primary amines, whereby said polybasic compounds are polycationic at physiological pH. Polysulfated glycans of the invention include but are not limited to heparin, heparan sulfate, dextran sulfate, chondroitin sulfate, dermatan sulfate or derivatives thereof.

The compositions of this invention specifically localize to sites of inflammation. These compositions may also bind to leukocytes, preferably monocytes and neutrophils and most preferably to neutrophils. For purposes of this invention, the term "bind to leukocytes" is intended to mean that the compositions of the invention are capable of accumulating at sites of infection or inflammation in mammalian body sufficient to allow detection of the accumulation of radiolabeled complexes prepared from the compositions as disclosed herein at sites of infection or inflammation by gamma scintigraphy.

In peptide embodiments of the scintigraphic imaging agents of the invention, preferred peptides include platelet factor 4 and peptides derived therefrom. For purposes of this invention, the term "peptides derived therefrom" is intended to encompass peptides having an amino acid sequence homologous to all or a portion of the platelet factor 4 amino acid sequence. Also intended to be circumscribed by this term are peptide fragments of platelet factor 4, whether generated by proteolytic degradation of native platelet factor 4 protein or by chemical synthesis of a portion of the platelet factor 4 amino acid sequence. Peptide fragments useful in the practice of this invention include those fragments capable of accumulating at sites of infection and inflammation in a mammalian body. Examples of such peptides are presented hereinafter in the Examples.

In Cp(aa)Cp-containing scintigraphic imaging agents, where Cp is a protected cysteine the S-protecting groups are the same or different and may be but not limited to:

—$CH_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);
—CH$_2$-(4-methoxyphenyl);
—CH-(4-pyridyl)(phenyl)$_2$;
—C(CH$_3$)$_3$
-9-phenylfluorenyl;
—CH$_2$NHCOR (R is unsubstituted or substituted alkyl or aryl);
—CH$_2$—NHCOOR (R is unsubstituted or substituted alkyl or aryl);
—CONHR (R is unsubstituted or substituted alkyl or aryl);
—CH$_2$—S—CH$_2$-phenyl.

Radiolabel binding moieties comprising cysteine-sulfur protecting groups designated "(pgp)$^S$", such as the bisamino, bisthiol moieties of the invention, are also described by the above-mentioned listing of protecting groups.

The preferred protecting group has the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl.

Labeling with Tc-99m is an advantage of the present invention because the nuclear and radioactive properties of this isotope make it an ideal component of a scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

Each polybasic peptide-containing embodiment of the invention is comprised of a sequence of amino acids. The term amino acid as used in this invention is intended to include all L- and D- amino acids, naturally occurring and otherwise. Reagents comprising polybasic peptides provided by the invention include but are not limited to the following (the amino acids in the following peptides are L-amino acids except where otherwise indicated):

acetyl-KC$_{Acm}$GC$_{Acm}$QAPLYKKIIKKLLES (SEQ ID No.:1)
acetyl-KKC$_{Acm}$GC$_{Acm}$QAPLYKKIIKKLLES (SEQ ID No.:2)
acetyl-KKKC$_{Acm}$GC$_{Acm}$QAPLYKKIIKKLLES (SEQ ID No.:3)
acetyl-KKKKC$_{Acm}$GC$_{Acm}$QAPLYKKIIKKLLES (SEQ ID No.:4)
acetyl-KKKKKC$_{Acm}$GC$_{Acm}$QAPLYKKIIKKLLES (SEQ ID No.:5)
acetyl-KC$_{Acm}$GC$_{Acm}$GGPLYKKIIKKLLES (SEQ ID No.:6)
acetyl-KKC$_{Acm}$GC$_{Acm}$GGPLYKKIIKKLLES (SEQ ID No.:7)
acetyl-KKKC$_{Acm}$GC$_{Acm}$GGPLYKKIIKKLLES (SEQ ID No.:8)
acetyl-KKKKC$_{Acm}$GC$_{Acm}$GGPLYKKIIKKLLES (SEQ ID No.:9)
acetyl-KKKKKC$_{Acm}$GC$_{Acm}$GGPLYKKIIKKLLES (SEQ ID No.:10)
acetyl-KKKKKKCGCGGPLYKKIIKKLLES (SEQ ID No.:11)
acetyl-KKKKKK.[BAT].GGPLYKKIIKKLLES (SEQ ID No.:12).

Polybasic peptide embodiments of the present invention may be chemically synthesized in vitro. Peptides of the present invention can generally advantageously be prepared on a peptide synthesizer. The peptides of this invention can be synthesized wherein the radiolabel binding moiety is covalently linked to the peptide during chemical in vitro synthesis, using techniques well known to those with skill in the art. Such peptides covalently-linked to the radiolabel binding moiety upon synthesis are advantageous because specific sites of covalent linkage can be determined therein.

Radiolabel binding moieties of the invention may be introduced into the target specific polybasic peptide during peptide synthesis. For embodiments [e.g., Pic-Gly-Cys (protecting group)-] comprising picolinic acid (Pic-), the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

This invention provides for the incorporation of these chelators into virtually any platelet factor 4-derived peptide, resulting in Tc-99m radiolabeled peptide components of the scintigraphic imaging agents of the invention.

This invention also provides polybasic, small, synthetic compounds which incorporate bisamine bisthiol (BAT) chelators which may be labeled with Tc-99m.

In forming a complex of radioactive technetium-99m with the reagents of this invention, the technetium complex, preferably a salt of Tc-99m pertechnetate, is reacted with the imaging agent in the presence of a reducing agent; in a preferred embodiment, the reducing agent is stannous chloride. Complexes and means for preparing such complexes are conveniently provided in a kit form comprising a first sealed vial containing a predetermined quantity of a reagent of the invention that is to be labeled and a sufficient amount of reducing agent to label the reagent with Tc-99m. Alternatively, the complex may be formed by reacting a reagent of the invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. Using either embodiment, the vial containing the unlabeled reagent and reducing agent can also advantageously contain the polysulfated glycan components of the compositions of the invention. The reaction of the scintigraphic imaging agents of this invention with Tc-99m pertechnetate or preformed Tc-99m labile complex can be carried out in an aqueous medium at room temperature. When an anionic complex is formed in an aqueous medium, the radiolabeled complex is in the form of a salt with a suitable cation such as sodium cation, ammonium cation, mono, di- or tri-lower alkyl amine cation, or any pharmaceutically acceptable cation.

In a preferred embodiment of the invention, a kit for preparing technetium-99m labeled peptides is provided. The peptide embodiments of the reagents of the invention can be chemically synthesized using methods and means well-known to those with skill in the art and described hereinbelow. An appropriate amount of such a reagent is introduced into a vial containing a reducing agent, such as stannous chloride or a solid-phase reducing agent, in an amount sufficient to label the agent with Tc-99m. An appropriate amount of a transfer ligand as described (such as tartrate, citrate, gluconate or mannitol, for example) can also be included. Technetium-99m labeled reagents according to the present invention can be prepared by the addition of an appropriate amount of Tc-99m or Tc-99m complex into the vials and reaction under conditions described in Example 2 hereinbelow. Said kits also comprise a second sealed vial containing an appropriate amount of a polysulfated glycan. Examples of efficacious polysulfated glycans include but are not limited to heparin, heparan sulfate, dextran sulfate, chondroitin sulfate, dermatan sulfate or derivatives thereof. Tc-99m labeled scintigraphic imaging agents of the invention can be prepared by mixing the Tc-99m labeled polybasic component from the first vial with the polysulfated glycan from the second vial.

Radioactively labeled scintigraphic imaging agents provided by the present invention are provided having a suitable amount of radioactivity. In forming the Tc-99m radioactive complexes, it is generally preferred to form radioactive complexes in solutions containing radioactivity at concentrations of from about 0.01 millicurie (mCi) to 100 mCi per ml.

Compositions comprising scintigraphic imaging agents comprised of technetium-99m labeled reagents and polysulfated glycans provided by this invention can be used for visualizing sites of inflammation, including abscesses and sites of "occult" infection. The Tc-99m labeled compositions can also be used for visualizing sites of inflammation caused by tissue ischemia, including such disorders as inflammatory bowel disease and arthritis. In accordance with this invention, the technetium-99m labeled compositions, wherein the reagents are provided either as a complex or as a salt with a pharmaceutically acceptable counterion, are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The composition to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.5 of an hour to permit the taking of scintiphotos. Any conventional method of scintigraphic imaging for diagnostic purposes can be utilized in accordance with this invention.

The technetium-99m labeled compositions of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

Alternatively, the invention provides methods for specifically radiolabeling whole blood and using such radiolabeled whole blood to image sites of inflammation within a mammalian body. In this embodiment of the invention, whole blood is mixed with an amount, from about 1 microgram to 100 milligrams, of a polysulfated glycan to form a mixture. Then an amount, from about 1 microgram to 100 milligrams, of a radiolabeled, preferably Tc-99m labeled, composition of matter that is a reagent comprising a polybasic moitey covalently linked to a radiolabel binding moiety, is added to form a radiolabeled mixture. This radiolabeled whole blood mixture is then administered to an animal such as a human being having or suspected of having a site of inflammation in uivo, and the radioactive signal detected to localize the site of inflammation as described herein. The requirement for antigenically-compatible, preferably but not necessarily autologous, heparinized whole blood to be used in this embodiment of the experiment will be understood by those skilled in the art.

The methods for making and labeling these compositions are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazoleor2-(1H-benzo-triazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides.

Where appropriate N-α-acetyl groups were introduced by treating the resin-bound peptide with acetic anhydride in N-methylpyrrolidinone (NMP).

Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or by electrospray mass spectroscopy (ESMS).

EXAMPLE 2

Preparation of Scintigraphic Imaging Agents

Peptide (1.0) prepared as in Example 1 was dissolved in 1.0 mL of phosphate buffered saline, 0.05M potassium phosphate buffer (pH 7.4) or water. Tc-99m gluceptate was prepared by reconstituting a Glucoscan vial (E.I. DuPont de Nemours, Inc.) with 1.0 mL of Tc-99m sodium pertechnetate containfing up to 200 mCi and allowed to stand for 15 minutes at room temperature. 250 µL of Tc-99m gluceptate was then added to the peptide reagent and the reaction allowed to proceed at 100° C. or at room temperature for 30 min and then filtered through a 0.2 µm filter.

The purity of the Tc-99m labeled peptide reagent was determined by HPLC under the conditions described in the footnotes of the following Table. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

TABLE I

| Peptides | FABMS MH⁺ | Radiochemical Yield | HPLC R₁ (min) |
|---|---|---|---|
| Ac-KKKKKCGCGGPLYKKIIKKLLES (SEQ ID No.: 11) | 2633 | 99% | 14.8 |
| Ac-KKKKKK.[BAT].GGPLYKKIIKKLLES (SEQ ID No.: 12) | 2778 | 97% | 15.6 |
| AcKKKKKC$_{Acm}$GC$_{Acm}$GGPLYKKIIKKLLES (SEQ ID No.: 10) | 2776 | 98% | 10.2, 11.3 |

Ac = acetyl;
Acm = acetamidomethyl;
single-letter abbreviations for amino acids can be found in G. Zubay, Biochemistry (2d. ed.), 1988 (MacMillen Publishing: New York) p.33.
General HPLC method:
solvent A = 0.1% CF3COOH/H2O
solvent B$_{90}$ = 0.1% CF$_3$COOH/90% CH$_3$CN/H$_2$O
solvent flow rate = 1.2 mL/min
Waters column = Waters Delta-Pak C18 5$\mu$ × 39 mm × 150 mm column
Method: Gradient elution  100% A to 100% B$_{90}$ in 10 min Scintigraphic imaging agents of the invention are prepared from such Tc-99m labeled peptides by the addition of a polysulfated glycan. For example, particular embodiments of the scintigraphic imaging agents of the invention are prepared by the addition of heparin to Tc-99m labeled peptides prepared as described above at a concentration of 0.1–10 mg peptide/1–200 mCi Tc-99m in a volume of 0.1–10 mL to a final concentration of about 10–100 USP Units heparin/mL.

EXAMPLE 3

Imaging and Biodistribution Using Tc-99m Labeled Scintigraphic Imaging Agents

The efficacy of scintigraphic imaging of inflammatory sites in vivo using the composition of the invention was demonstrated as follows. New Zealand white rabbits were innoculated intramuscularly in the left calf with a potent strain of *Escherichia coli*. After 24 h, the animals were sedated by intramuscular injection with ketamine and xylazine. The animals were then injected intravenously with Tc-99m labeled peptide ($\leq$150 $\mu$g peptide/2–10 mCi Tc-99m) alone or in a solution that contained 30 U.S.P. Units/mL heparin. The animals were positioned supine in the field of view of a gamma camera (LEAP collimator, photopeaked for Tc-99m) and imaged over the first hour post-injection, and then at approximately 1h intervals over the following 3 h or 13 h. Animals were allowed to recover between the times of image acquisition and re-anestetized as needed.

Upon completion of the final imaging, each animal was sacrificed by phenobarbital overdose induced by i.v. injection, and dissected to obtain samples of blood and of infected and control muscle. These tissue samples were weighed and counted using a gamma counter. A standard amount of the injected dose was also counted in this manner. The percent injected dose (per gram of tissue) remaining in the tissue was calculated from the results of gamma counting. Ratios of percent injected dose per gram of infected versus non-infected muscle tissue, and ratios of percent of injected dose per gram of infected tissue versus blood, were calculated; these results are shown in the following Table.

Rabbits were injected with Tc-99m labeled imaging agents of the invention, having formulae:

acetyl-KKKKKC$_{Acm}$GC$_{Acm}$GGPLYKKIIKKLLES (P322) (SEQ ID No.:10), acetyl-KKKKKCGCGGPLYKKIIKKLLES (P483) (SEQ ID No.:11), and acetyl-KKKKKK.[BAT].GGPLYKKIIKKLLES (P514) (SEQ ID No.:12).

The combination of Tc-99m labeled peptide and heparin resulted in a greater percentage of the injected dose detected in the infected muscle, and higher ratios of infected muscle/blood and infected muscle to normal muscle, than were obtained using the labeled peptide alone (see Table II).

TABLE II

| Composition | % ID/g: infected muscle | | % ID/g: normal muscle | | % ID/g: blood | | infected muscle/blood | | infected muscle/ normal muscle | |
|---|---|---|---|---|---|---|---|---|---|---|
| | 4 h | 14 h | 4 h | 14 h | 4 h | 14 h | 4 h | 14 h | 4 h | 14 h |
| P483 | 0.021 | N.T. | 0.007 | N.T. | 0.055 | N.T. | 0.39 | N.T. | 3.2 | N.T. |
| P483 + Heparin | 0.063 | N.T. | 0.003 | N.T. | 0.023 | N.T. | 3.0 | N.T. | 25.0 | N.T. |
| P514 + Heparin | 0.095 | N.T. | 0.009 | N.T. | 0.050 | N.T. | 1.9 | N.T. | 10.0 | N.T. |
| P322 | 0.013 | 0.007 | 0.003 | 0.001 | 0.018 | 0.006 | 0.70 | 1.2 | 4.9 | 7.0 |
| P322 + heparin | 0.019 | 0.018 | 0.004 | 0.001 | 0.015 | 0.010 | 1.2 | 1.9 | 5.0 | 18.0 |

N.T. = Not tested

EXAMPLE 4

Imaging In Vivo in Humans Using Tc-99m Labeled Scintigraphic Imaging Agents

The efficacy of scintigraphic imaging of inflammatory sites in vivo in humans using P322H was determined. P322H is a scintigraphic imaging agent prepared by adding heparin to a final concentration of 30 U/mL to 10–20 mCi Tc-99m labeled P322 peptide (comprising about 1 mg peptide), having the formula:

acetyl-KKKKKC$_{Acm}$GC$_{Acm}$GGPLYKKIIKKLLES (SEQ ID No.:10).

This scintigraphic imaging agent was tested in 4 human patients, each of whom had sites of infection that were confirmed using conventional diagnostic techniques (including computer-assisted tomography, surgery and/or clinical presentation).

Each patient was administered 10–20 mCi Tc-99m/P322H by intravenous injection. Gamma scintigraphy was started simultaneously with injection, and anterior and posterior scintigraphic images were then acquired over approximately two hours post-injection using a large filed-of-view gamma camera equipped with a high resolution collimator (photopeaked at 140 keV, with a ±20% window).

Figure 1:
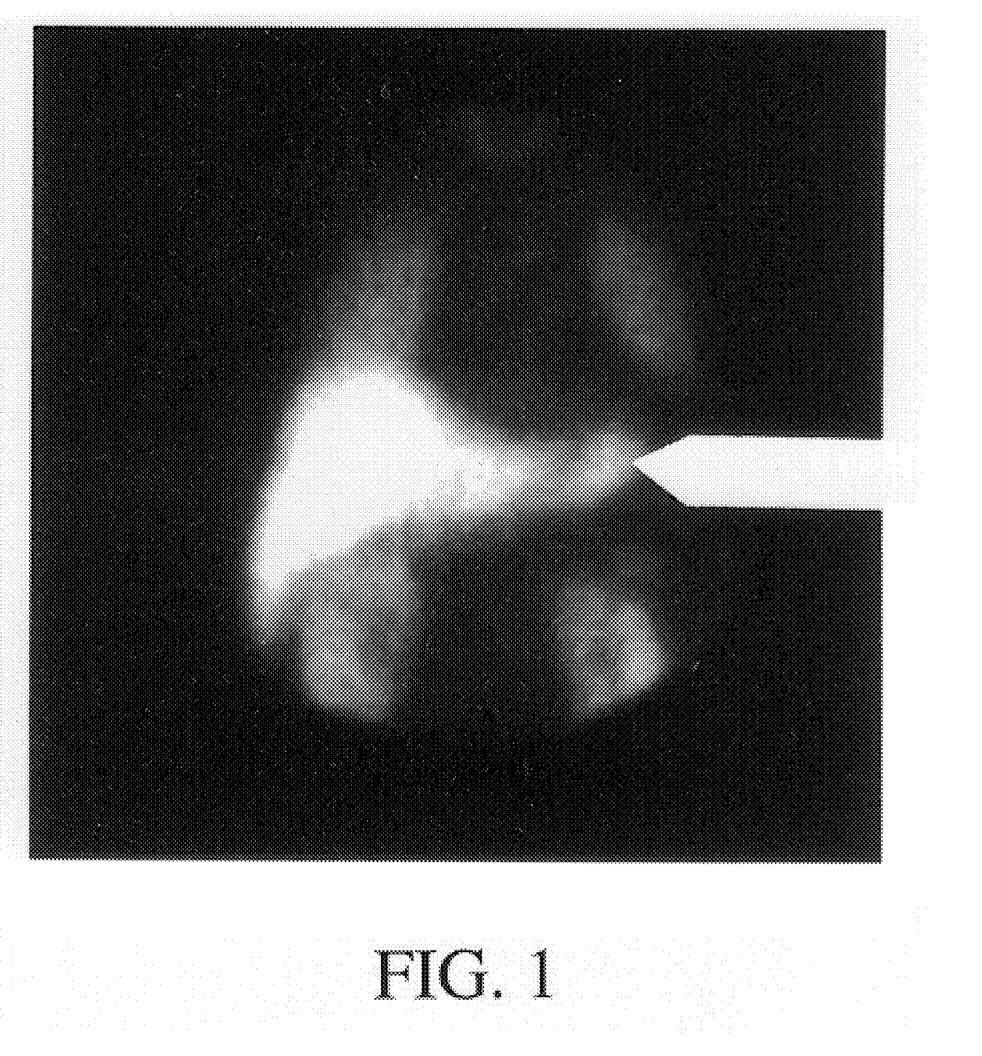
FIG. 1 illustrates in vivo scintigraphic imaging of a human patient bearing a splenic bed abscess in a patient 8 weeks post-splenectomy using Tc-99m/P322H scintigraphic imaging agent of the invention.

Initially, a high degree of imaging activity was observed in the lung, which activity decreased substantially over the course of the study. Spleen, liver and bone marrow uptake were also observed. Diagnoses of deep thigh abscess, appendicitis, peritonitis and splenic bed abscess were made from the Tc-99m/P322H imaging scans; these diagnoses were consistent with confirmatory diagnoses made on other grounds. An example of one such imaging scan is shown in FIG. 1, in which the splenic bed abscess in one patient has been successfully imaged. The arrow points to the image of a splenic bed abscess in a patient 8 weeks post-surgical removal of the patient's spleen.

These studies illustrate the utility of the scintigraphic imaging agents of the invention for in vivo ascintigraphic imaging in humans.

It should be understood that the foregoing disclosure emphasizes certain specific embodiments of the invention and that all modifications or alternatives equivalent thereto are within the spirit and scope of the invention as set forth in the appended claims.

What is claimed is:

1. A composition comprising:

a) a reagent comprising:
      i) a polybasic compound having a molecular weight from about 500 daltons to about 15,000 daltons and having at least 5 chemical functionalities that are basic at physiological pH; and
      ii) a technetium-99m binding moiety covalently linked to the compound; and
   b) a polysulfated glycan having a molecular weight of at least about 1,000 daltons;

wherein the composition is capable of accumulating at sites of inflammation in vivo.

2. The composition of claim 1, wherein the chemical functionalities are amines.

3. The composition of claim 1, wherein the polybasic compound is a peptide of 5 to 100 amino acids.

4. The composition of claim 3, wherein the peptide is platelet factor 4 or a fragment thereof.

5. The composition of claim 4, wherein the peptide comprises an amino acid sequence PLYKKIIKKLLES (SEQ ID NO:13) or KKIIKKILES (SEQ ID NO:14).

6. The composition of claim 5, wherein the peptide has an amino acid selected from the group consisting of acetyl-KKKKKCGCGGPLYKKIIKKLLES (SEQ ID NO:11) and acetyl-KKKKKK.[BAT].GGPLYKKIIKKLLES (SEQ ID NO:12).

7. The composition of claim 6, having the formula:

acetyl-KKKKKCGCGGPLYKKIIKKLLES (SEQ ID NO:12).

8. The composition of claim 7, wherein the polysulfated glycan is heparin.

9. The composition of claim 1, wherein the polysulfated glycan is heparin, heparan sulfate, dextran sulfate, chondroitin sulfate, dermatan sulfate or a derivative thereof.

10. The composition of claim 1, wherein the technetium-99m binding moiety is selected from the group consisting of:

$$Cp(aa)Cp \qquad\qquad I.$$

wherein Cp is a protected or unprotected cysteine and (aa) is an amino acid;

a technetium-99m bonding moiety comprising a single thiol moiety having a formula:

$$A-CZ(B)-[C(R^1R^2)]_n-X \qquad\qquad II.$$

wherein

A is H, HOOC, $H_2$NOC, (peptide)-NHOC, (peptide)-OOC or $R^4$;

B is H, SH, —$NHR^3$, —$N(R^3)$-(peptide), or $R^4$;

X is H, SH, —$NHR^3$, —$N(R^3)$-(peptide) or $R^4$;

Z is H or $R^4$;

$R^1$, $R^2$, $R^3$ and $R^4$ are independently H or lower straight or branched chain or cyclic alkyl;

n is 0, 1 or 2;

and where B is —$NHR^3$ or —$N(R^3)$-(peptide), X is SH, and n is 1 or 2;

where X is —$NHR^3$ or —$N(R^3)$-(peptide), B is SH, and n is 1 or 2;

where B is H or $R^4$, A is HOOC, $H_2$NOC, (peptide)-NHOC, (peptide)-OOC, X is SH, and n is 0 or 1;

where A is H or $R^4$, then where B is SH, X is —$NHR^3$ or —$N(R^3)$-(peptide) and where X is SH, B is —$NHR^3$ or —$N(R^3)$-(peptide);

where X is H or $R^4$, A is HOOC, $H_2$NOC, (peptide)-NHOC, (peptide)-OOC and B is SH;

where Z is methyl, X is methyl, A is HOOC, $H_2$NOC, (peptide)-NHOC, (peptide)-OOC, B is SH and n is 0;

and wherein the thiol moiety is in the reduced form;

wherein
X=H or a protecting group;
(amino acid)=any amino acid;

wherein
X=H or a protecting group;
(amino acid)=any amino acid;

wherein
each $R^5$ is independently H, $CH_3$ or $C_2H_5$;
each $(pgp)^S$ is independently a thiol protecting group or H;
m, n and p are independently 2 or 3;
A=linear or cyclic lower alkyl, aryl, heterocyclyl, a combination thereof or a substituted derivative thereof;

wherein
each $R^5$ is independently H, lower alkyl having 1 to 6 carbon atoms, phenyl, or phenyl substituted with lower alkyl or lower alkoxy;
m, n and p are independently 1 or 2;
A=linear or cyclic lower alkyl, aryl, heterocyclyl, a combination thereof or a substituted derivative thereof;
V=H or —CO-peptide;
$R^6$=H or peptide;
and wherein when V=H, $R^6$=peptide and when $R^6$=H, V=—CO-peptide.

11. The composition of claim 1, wherein the polybasic compound and the technetium-99m binding moiety are covalently linked through from about one to about twenty amino acids.

12. The composition of claim 10, wherein the technetium-99m binding moiety is Cp(aa)Cp and Cp is a protected cysteine having a protecting group of formula wherein R is a lower alkyl having 1 to 6 carbon atoms, 2-pyridyl, 3-pyridyl, 4-pyridyl, phenyl, or phenyl substituted with lower alkyl, hydroxy, lower alkoxy, carboxy, or lower alkoxycarbonyl.

13. The composition of claim 10, wherein the technetium-99m-binding moiety has a formula:

14. A kit for preparing a radiopharmwoutical preparation, said kit comprising
a) a fist sealed vial containing a predetermined quantity of a reagent comprising:
   i) a polybasic compound having a molecular weight from about 500 daltons to about 15,000 daltons and having at least 5 chemical functionalities that are basic at physiological pH;
   ii) a technetium-99m binding moiety covalently linked to the compound; and
   iii) a sufficient amount of a reducing agent to label the reagent with technetium-99m; and
b) a second sealed vial containing a predetermined quantity of a polysulfated glycan having a molecular weight of at least about 1,000 daltons.

15. The kit of claim 14, wherein the reducing agent is selected from the group of a dithionite ion, a stannous ion, and a ferrous ion.

16. The kit of claim 14, wherein the reagent is acetyl-KKKKKCGCGGPLYKIIKKLLES (SEQ ID NO:12) and the polysulfated glycan is heparin.

17. The composition of claim 1, further comprising technetium-99m.

18. A method of imaging a site of inflammation within a mammalian body comprising the steps of administering an effective diagnostic amount of the composition of claim 17 and detecting a radioactive signal from the Tc-99m localized at said site.

19. The method of claim 18, wherein the polybasic compound is acetyl-KKKKKCGCGGPLYKKIILLES (SEQ ID NO:12) and the polysulfated glycan is heparin.

20. A method of imaging a site of inflammation within a mammalian body comprising the steps of:
a) mixing whole blood and from about 1 microgram to 100 milligrams of the composition of claim 17 to form a radiolabeled mixture;
b) administering said mixture to a mammal; and
c) detecting a radioactive signal from the technetium-99m localized at said site.

21. The method of claim 20, wherein the polybasic compound is acetyl-KKKKKCGCGGPLYKKIIKKLLES (SEQ ID NO:12) and the polysulfated glycan is heparin.

22. A process for preparing a reagent comprising:
i) a polybasic compound having a molecular weight from about 500 daltons to about 15,000 daltons and having at least 5 chemical functionalities that are basic at physiological pH; and
ii) a technetium-99m binding moiety covalently linked to the compound; by in vitro chemical synthesis.

23. The process of claim 22, wherein the polybasic compound is a peptide and the synthesis is solid phase peptide synthesis.

24. The process of claim 22, wherein the technetium-99m binding moiety is covalently linked to the peptide during solid phase peptide synthesis.

25. The composition of claim 6, further comprising technetium-99m.

26. The composition of claim 6, further comprising technetium-99m.

27. A pharmaceutical composition comprising the composition of claim 1 and a pharmaceutically-acceptable carrier.

28. A pharmaceutical composition comprising the composition of claim 8 and a pharmaceutically-acceptable carrier.

29. A composition comprising:
   a) a multimeric reagent comprising
      i) at least two polybasic compounds, each having a molecular weight from about 500 daltons to about 15,000 daltons and having at least 5 chemical functionalities that are basic at physiological pH,
      ii) a technetium-99m binding moiety covalently linked to each compound; and
      iii) a polyvalent linking moiety covalently linked to each compound and to each technetium-99m binding moiety; and
   b) a polysulfated glycan having a molecular weight of at least about 1,000 daltons.

30. The composition of claim 29, wherein the polyvalent linking moiety is bis-succinimidylmethylether, 4-(2,2-dimethylacetyl)benzoic acid, N-[2-(N'N'-bis(2-succinimdo-ethyl)aminoethyl)]-$N^6$,$N^9$-bis(2-methyl-2-mercaptopropyl)-6,9-diazanonanamide, tris(succinimidylethyl)amine, bis-succinimidohexane, 4-(O—$H_2$CO-Gly-Gly-Cys.amide) acetophenone, tris(acetamidoethyl)amine, bis(acetamidomethyl)amine, bis(acetamidoethyl)amine, α,ε-bis(acetyl)lysine, lysine, 1,8-bis-acetamido-3,6-dioxa-octane, a derivative of bis-succinimidylmethylether, a derivative of 4-(2,2-direthylacetyl)benzoic acid, a derivative of N-[2-(N',N'-bis(2-succinimido-ethyl)aminoethyl)]-$N^6$, $N^9$-bis(2-methyl-2-mercaptopropyl)-6,9-diazanonanamide, a derivative of tris(succinimidylethyl)amine, bis-succinimidohexane, a derivative of 4-(O—$CH_2$CO-Gly-Gly-Cys.amide)acetophenone, a derivative of tris(acetamidoethyl)amine, a derivative of bis(acetamidomethyl)amine, a derivative of bis(acetamidoethyl)amine, a derivative of α,ε-bis(acetyl) lysine, a derivative of lysine, or a derivative of 1,8-bis-acetamido-3,6dioxa-octane.

* * * * *

```
                       SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
         (A) LENGTH: 19 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1..4
         (D) OTHER INFORMATION: /label= MODIFIED-CYS
             /note= "The thiol group of each cysteine is
             protected by an acetamidomethyl group; the amino
             terminal amine is acetylated."

(xi) SEQUENCE DESCRIPTION: SEQ ID NO:1:

Lys Cys Gly Cys Gln Ala Pro Leu Tyr Lys Lys Ile Ile Lys Lys Leu Leu
1               5                  10                  15

Glu Ser (2) INFORMATION FOR SEQ ID NO:2:

(i) SEQUENCE CHARACTERISTICS:
         (A) LENGTH: 20 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1..5
         (D) OTHER INFORMATION: /label= MODIFIED-CYS
             /note= "The thiol group of each cysteine is
             protected by an acetamidomethyl group; the amino
             terminal amine is acetylated."

(xi) SEQUENCE DESCRIPTION: SEQ ID NO:2:
```

```
Lys Lys Cys Gly Cys Gln Ala Pro Leu Tyr Lys Ile Ile Lys Lys Leu
1               5                   10                  15

Leu Glu Ser
        20
```

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1..6
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:3:

```
Lys Lys Lys Cys Gly Cys Gln Ala Pro Leu Tyr Lys Lys Ile Ile Lys Lys
1               5                   10                  15

Leu Leu Glu Ser
        20
```

(2) INFORMATION FOR SEQ ID NO:4:

(i) SEQUENCE CHARACTERISTICS:
        (A) LENGTH: 22 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1..7
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:4:

```
Lys Lys Lys Lys Cys Gly Cys Gln Ala Pro Leu Tyr Lys Lys Ile Ile Lys
1               5                   10                  15

Lys Leu Leu Glu Ser
        20
```

(2) INFORMATION FOR SEQ ID NO:5:

(i) SEQUENCE CHARACTERISTICS:
        (A) LENGTH: 23 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1..8
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:5:

```
Lys Lys Lys Lys Lys Cys Gly Cys Gln Ala Pro Leu Tyr Lys Lys Ile Ile
1               5                   10                  15

Lys Lys Leu Leu Glu Ser
            20
```

(2) INFORMATION FOR SEQ ID NO:6:

(i) SEQUENCE CHARACTERISTICS:
        (A) LENGTH: 19 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1..4
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:6:

```
Lys Cys Gly Cys Gly Gly Pro Leu Tyr Lys Lys Ile Ile Lys Lys Leu Leu
1               5                   10                  15

Glu Ser
```

(2) INFORMATION FOR SEQ ID NO:7:

(i) SEQUENCE CHARACTERISTICS:
        (A) LENGTH: 20 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1..5
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:7:

```
Lys Lys Cys Gly Cys Gly Gly Pro Leu Tyr Lys Lys Ile Ile Lys Lys Leu
1               5                   10                  15

Leu Glu Ser
        20
```

(2) INFORMATION FOR SEQ ID NO:8:

(i) SEQUENCE CHARACTERISTICS:
        (A) LENGTH: 21 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1..6
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:8:

```
Lys Lys Lys Cys Gly Cys Gly Gly Pro Leu Tyr Lys Lys Ile Ile Lys Lys
1               5                   10                  15
```

```
Leu Leu Glu Ser
        20

(2) INFORMATION FOR SEQ ID NO:9:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..7
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:9:

Lys Lys Lys Lys Cys Gly Cys Gly Gly Pro Leu Tyr Lys Lys Ile Ile Lys
1               5                   10                  15

Lys Leu Leu Glu Ser
        20

(2) INFORMATION FOR SEQ ID NO:10:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..8
        (D) OTHER INFORMATION: /label= MODIFIED-CYS
            /note= "The thiol group of each cysteine is
            protected by an acetamidomethyl group; the amino
            terminal amine is acetylated."

(xi) SEQUENCE DESCRIPTION: SEQ ID NO:10:

Lys Lys Lys Lys Lys Cys Gly Cys Gly Gly Pro Leu Tyr Lys Lys Ile Ile
1               5                   10                  15

Lys Lys Leu Leu Glu Ser
        20

(2) INFORMATION FOR SEQ ID NO:11:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..2
        (D) OTHER INFORMATION: /label= Acetyl
            /note= "The amino terminus is acetylated."

(xi) SEQUENCE DESCRIPTION: SEQ ID NO:11:

Lys Lys Lys Lys Lys Cys Gly Cys Gly Gly Pro Leu Tyr Lys Lys Ile Ile
1               5                   10                  15

Lys Lys Leu Leu Glu Ser
        20
```

-continued (2) INFORMATION FOR SEQ ID NO:12:

(i) SEQUENCE CHARACTERISTICS:
        (A) LENGTH: 21 amino acids
        (B) TYPE: amino acid
        (D) TOPOLOGY: linear    (ii) MOLECULE TYPE: peptide    (ix) FEATURE:
        (A) NAME/KEY: Modified-site
        (B) LOCATION: 1
        (D) OTHER INFORMATION: /label= Acetyl
            /note= "The amino terminus is acetylated."

(ix) FEATURE:
        (A) NAME/KEY: Modified-site
        (B) LOCATION: 6
        (D) OTHER INFORMATION: /label= BAT
            /note= "The side chain amino group of lysine is
            modified by covalent linkage to a BAT group."

(xi) SEQUENCE DESCRIPTION: SEQ ID NO:12:

Lys Lys Lys Lys Lys Lys Gly Gly Pro Leu Tyr Lys Lys Ile Ile Lys Lys
1              5                    10                  15

Leu Leu Glu Ser
        20